(12) United States Patent
Cinbis (10) Patent No.: US 10,905,810 B2
(45) Date of Patent: Feb. 2, 2021

(54) TETS RECHARGED PATIENT ALERT SYSTEM FOR LVAD PATIENTS

(71) Applicant: Medtronic, Inc., Minneapolis, MN (US)

(72) Inventor: Can Cinbis, Salt Lake City, UT (US)

(73) Assignee: Medtronic, Inc., Minneapolis, MN (US)

( * ) Notice: Subject to any disclaimer, the term of this patent is extended or adjusted under 35 U.S.C. 154(b) by 109 days.

(21) Appl. No.: 16/280,221

(22) Filed: Feb. 20, 2019

(65) Prior Publication Data

US 2019/0255237 A1    Aug. 22, 2019

Related U.S. Application Data

(60) Provisional application No. 62/633,209, filed on Feb. 21, 2018.

(51) Int. Cl.
| | | |
|---|---|---|
| *A61M 1/12* | (2006.01) | |
| *H02J 7/02* | (2016.01) | |
| *H02J 50/10* | (2016.01) | |
| *A61M 1/10* | (2006.01) | |

(52) U.S. Cl.
CPC ........... *A61M 1/127* (2013.01); *A61M 1/101* (2013.01); *A61M 1/122* (2014.02); *H02J 7/025* (2013.01); *H02J 50/10* (2016.02); *A61M 2205/18* (2013.01); *A61M 2205/581* (2013.01); *A61M 2205/582* (2013.01); *A61M 2205/583* (2013.01);
(Continued)

(58) Field of Classification Search
CPC ...... A61M 1/101; A61M 1/122; A61M 1/127; A61M 2205/18; A61M 2205/581; A61M 2205/582; A61M 2205/583; A61M 2205/8212; A61M 2205/8243; A61M 2205/8287; H02J 50/025; H02J 50/10
USPC ............................................. 300/16–18, 300
See application file for complete search history.

(56) References Cited

U.S. PATENT DOCUMENTS

| | | | |
|---|---|---|---|
| 8,203,657 | B2 | 6/2012 | Vitito |
| 9,707,327 | B2 | 7/2017 | Heilman et al. |

(Continued)

FOREIGN PATENT DOCUMENTS

| | | | |
|---|---|---|---|
| EP | 3131601 B1 | 7/2018 | |

OTHER PUBLICATIONS

International Search Report and Written Opinion dated Apr. 30, 2019, for corresponding International Application No. PCT/US2019/018676; International Filing Date: Feb. 20, 2019 consisting of 15 pages.

*Primary Examiner* — Carl H Layno
*Assistant Examiner* — Jane C Kalinock
(74) *Attorney, Agent, or Firm* — Christopher & Weisberg, P.A.

(57) ABSTRACT

A medical implant information reporting device and method of charging the same, the reporting device having an integrated harvesting coil configured to couple energy from an electromagnetic field of a source coil to induce current in the harvesting coil, are provided. According to one aspect, a method includes electrically coupling the harvesting coil to the source coil to charge the medical implant information reporting device, the source coil being sized to be removably disposed one of on and around the torso of a patient and configured to inductively power a medical implant about which the medical implant information reporting device reports.

19 Claims, 7 Drawing Sheets

(52) U.S. Cl.
CPC ............... *A61M 2205/8212* (2013.01); *A61M 2205/8243* (2013.01)

(56) References Cited

U.S. PATENT DOCUMENTS

| | | | |
|---|---|---|---|
| 2013/0053624 A1* | 2/2013 | Zilbershlag | H01F 7/0247 600/16 |
| 2014/0175898 A1* | 6/2014 | Kurs | B60L 53/36 307/104 |
| 2014/0275727 A1 | 9/2014 | Bonde et al. | |
| 2014/0306654 A1* | 10/2014 | Partovi | H02J 50/12 320/108 |
| 2015/0236546 A1 | 8/2015 | Kesler et al. | |
| 2016/0022888 A1 | 1/2016 | Heilman et al. | |
| 2016/0056664 A1* | 2/2016 | Partovi | B60L 53/124 307/104 |
| 2017/0063143 A1 | 3/2017 | Hoarau et al. | |
| 2017/0304515 A1 | 10/2017 | Heilman et al. | |
| 2018/0083473 A1* | 3/2018 | Menegoli | H02J 7/025 |
| 2018/0126053 A1* | 5/2018 | Zilbershlag | A61M 1/122 |

\* cited by examiner

| INPUT PARAMETERS | NOM | MIN | MAX |
|---|---|---|---|
| ☐ Excitation coil supply peak (V) | 36.315 | 5 | 20 |
| ☐ Supply source resistance (ohms) | 0.001 | 1e-05 | 1 |
| ☐ Excitation coil # of turns | 10 | 1 | 20 |
| ☐ Excitation coil outer diameter (m) | 0.5 | 0.03 | 0.06 |
| ☐ Excitation coil width (m) | 0.05 | 0.0005 | 0.0015 |
| ☐ Excitation coil wire diameter (m) | 0.0015 | 0.0005 | 0.0015 |
| ☐ Excitation coil wire spacing (m) | 0.002 | 1e-05 | 0.001 |
| ☐ Excitation coil layer spacing (m) | 0.002 | 0.0002 | 0.005 |
| ☐ Excitation coil wire resistivity (ohms-m) | 1.667e-08 | 1e-09 | 2e-08 |
| ☐ Excitation coil tuning cap (F) | 3e-07 | 2e-07 | 4e-07 |
| ☑ Load coil # of turns | 30 | 5 | 50 |
| ☐ Load coil outer diameter (m) | 0.0448 | 0.015 | 0.043 |
| ☐ Load coil width (m) | 0.005 | 5e-05 | 0.02 |
| ☐ Load coil wire diameter (m) | 0.0002 | 1e-05 | 0.002 |
| ☐ Load coil wire spacing (m) | 0.0002 | 1e-05 | 0.002 |
| ☐ Load coil layer spacing (m) | 0.0002 | 0.0001 | 0.003 |
| ☐ Load coil wire resistivity (ohms-m) | 1.66e-08 | 1e-08 | 2e-08 |
| ☐ Load tuning cap (F) | 3e-07 | 2e-07 | 4e-07 |
| ☐ Load coil load (ohms) | 1000 | 100 | 5000 |
| ☐ Effective rel. permeability | 1 | 1 | 2 |
| ☐ Distance between coils (m) | 1.335 | 0.005 | 0.025 |
| ☐ Frequency of operation (Hz) | 100000 | 10000 | 1000000 |
| ☐ Radial coordinate for H-field (m) | 0 | 1e-06 | 0.3 |
| ☐ Axial coordinate for H-field (m) | 0.22 | -0.1 | 0.4 |
| # of variable points | 46 | ☑ Optimize tuning cap 1 | |
| Sweep style | Linear | ☑ Optimize tuning cap 2 | |
| Plot color | Blue | ☐ Hold plots | |
| Number of coils | 2 | LOAD DATA | |
| TX/RX resonance code | Series/Parall... | SAVE DATA | |

TETS RECHARGED PATIENT ALERT SYSTEM FOR LVAD PATIENTS

CROSS-REFERENCE TO RELATED APPLICATION

This application claims the benefit of U.S. Application Ser. No. 62/633,209, filed Feb. 21, 2018.

FIELD

The present invention relates to a method and system for charging a medical implant information reporting device.

BACKGROUND

In certain disease states, the heart lacks sufficient pumping capacity to meet the needs of the body. This inadequacy can be alleviated by providing a mechanical pumping device referred to as a ventricular assist device ("VAD") to supplement the pumping action of the heart. Considerable effort has been devoted to providing a VAD which can be implanted and which can remain in operation for months or years to keep the patient alive while the heart heals, or which can remain in operation until a suitable donor heart becomes available if the heart does not heal.

The VAD is typically connected to the heart, most commonly to the left ventricle. For example, a VAD may include a pump which is implanted in the body outside of the heart. The VAD may have an inlet cannula connected to the interior of the left ventricle and connected to the intake of the pump. The VAD may also include an outlet tube connected between the outlet of the pump and the aorta. Once connected, the VAD and the heart both pump blood from the left ventricle to the aorta.

One investigational method and system for powering the VAD is a transcutaneous energy transfer or "TET" device. Such a device includes an implantable induction coil. The implantable unit typically is mounted remote from the heart, for example, underneath the patient's skin. Energy is supplied to the induction coil of the implantable unit by a source coil incorporated in an external unit worn by the patient. An internal battery provides continued operation during intervals when the patient is not wearing the external unit.

SUMMARY

The techniques of this disclosure generally relate to a method and system for charging a medical implant information reporting device.

In one aspect, a method for charging a medical implant information reporting device having an integrated harvesting coil configured to couple energy from an electromagnetic field of a source coil to induce current in the harvesting coil includes electromagnetically coupling the harvesting coil to the source coil to charge the medical implant information reporting device, the source coil being sized to be removably disposed one of on and around a torso of a patient and configured to inductively power a medical implant about which the medical implant information reporting device reports.

In another aspect, the source coil is configured to charge the medical implant information reporting device at a distance between the source coil and the harvesting coil exceeding 5 centimeters.

In another aspect, the source coil is configured to charge the medical implant information reporting device at a distance between the source coil and the harvesting coil exceeding 1 meter.

In another aspect, the source coil generates power to produce an electromagnetic field having a magnetic field strength exceeding 15 microTesla at the harvesting coil of the medical implant information reporting device.

In another aspect, the harvesting coil is configured to generate more than 15 milli-Watts of power delivered to a 1 kilo-ohm load.

In another aspect, the harvesting coil has from 5 to 200 turns and an outer diameter from 1 to 6 centimeters.

In another aspect, the medical implant information reporting device is wearable as one from the group consisting of a watch on a wrist, a pendant that hangs from a neck, and an armband worn over an upper arm of a patient having the medical implant.

In one aspect, a medical implant information reporting device having an integrated harvesting coil configured to couple energy from an electromagnetic field of a source coil to induce current in the harvesting coil includes at least one of a display configured to display information about a medical implant and a speaker configured to provide acoustic messages about the medical implant or vibrate to alert patient to an impending condition of the LVAD system. The harvesting coil is embedded in the medical implant information reporting device and is configured to couple energy from the source coil to charge a battery of the medical implant information reporting device.

In another aspect, the harvesting coil is configured to receive power to charge the medical implant information reporting device at a distance between the source coil and the harvesting coil exceeding ½ meter.

In another aspect, the harvesting coil is configured to charge the medical implant information reporting device when receiving an electromagnetic field having a magnetic field strength not exceeding 15 micro-Tesla at the harvesting coil of the medical implant information reporting device.

In another aspect, the harvesting coil is configured to generate more than 15 milli-Watts of power delivered to a 1 kilo-ohm load.

In another aspect, the harvesting coil has from 5 to 200 turns and an outer diameter from 1 to 6 centimeters to achieve coupling of energy from the source coil to charge the battery.

In another aspect, the medical implant information reporting device is wearable as one from the group consisting of a watch on a wrist, a pendant that hangs from a neck and an armband worn around an upper arm of a patient with the implantable medical device.

In one aspect, a medical implant information reporting device configured for operation with a transcutaneous electrical transmission subsystem (TETS) of a ventricular assist device (VAD), the TETS having a source coil configured to provide energy to the VAD includes a harvesting coil integrated with the reporting device, the harvesting coil having a plurality of turns, diameter, and conductor thickness to couple energy from the source coil of the TETS to charge a battery of the reporting device. A rechargeable battery is configured to be recharged by current from the harvesting coil. At least one of a display configured to display information concerning the VAD and a speaker to provide acoustic information concerning the VAD is included.

In another aspect, the source coil is configured to provide power to the VAD.

In another aspect, the speaker is further configured to sound an alert if the charge of the battery is less than a threshold.

In another aspect, the harvesting coil is configured to provide power to the reporting device to enable an average power consumption by the reporting device exceeding 8 milli-Watts.

In another aspect, the reporting device presents to the harvesting coil an effective load resistance of between 0.8 to 10 kilo-Ohms.

In another aspect, the battery is rechargeable when a distance is between the source coil and the harvesting coil exceeds 5 centimeters.

In another aspect, the reporting device is one of a watch a pendant and an armband.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of apparatus components and processing steps related to charging a medical implant information reporting device. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
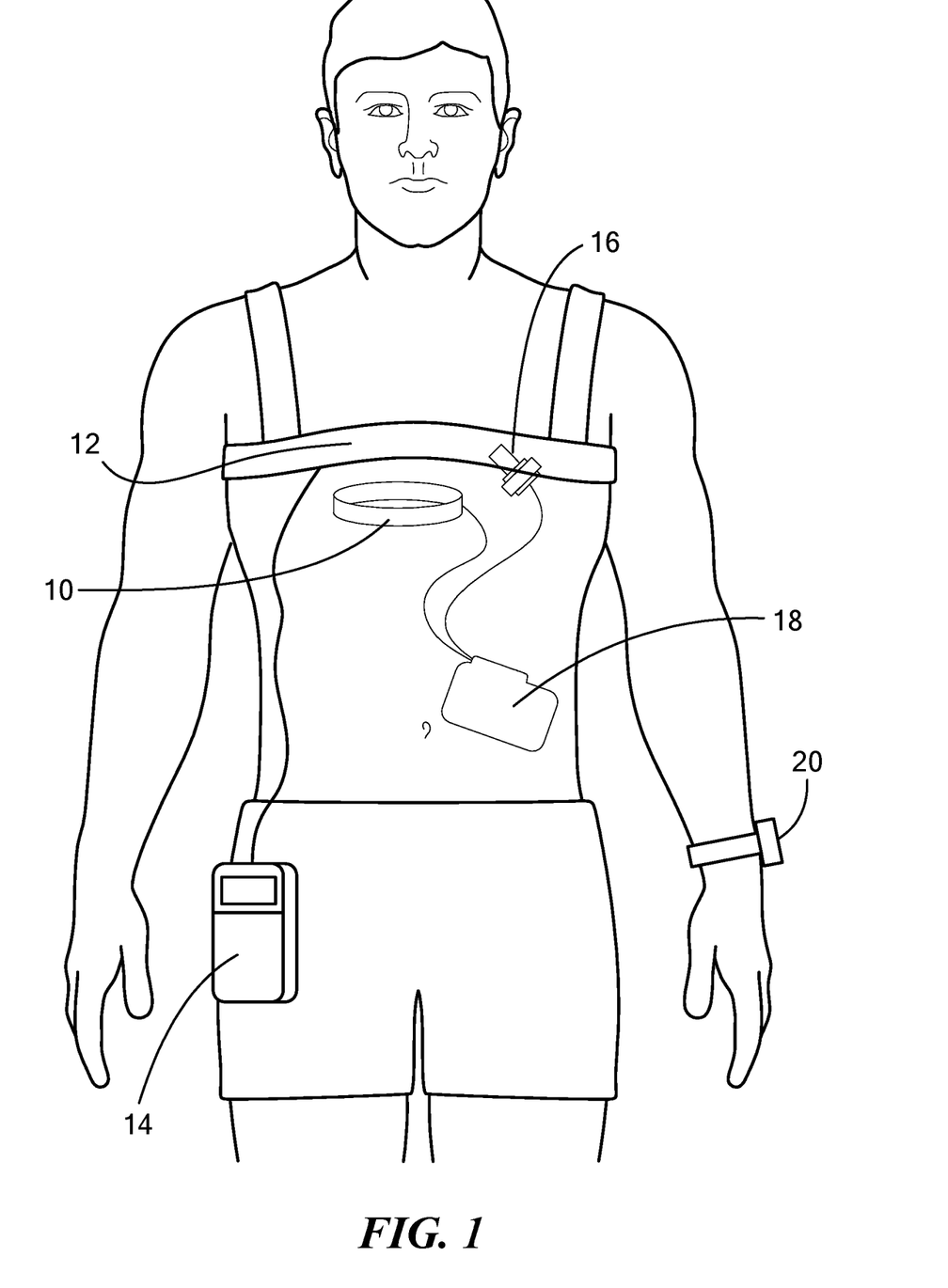
FIG. 1 depicts a first configuration of a TETS with a medical implant information reporting device worn as a watch.

Embodiments are directed to charging a medical implant information reporting device via the electromagnetic energy generated by a source coil that is part of a transcutaneous energy transfer system (TETS) for a patient having a ventricle assistance device (VAD). FIG. 1 illustrates a first configuration of a TETS with a medical implant information reporting device worn as a watch. The TETS has an implanted coil 10 implanted within the body and an external source coil 12 positioned outside the body and, in this example, worn around the torso of the patient. An external controller and battery 14 may be worn at the waist of the patient, for example, attached to a belt of a patient or other portable carrying equipment. This controller provides regulated power to the external coil 12, which induces power in the implanted internal coil 10, which in turn powers an implanted VAD pump 16 or other implanted device. The implant device 16 may be controlled internally by an implanted controller and battery 18. The medical implant information reporting device 20 is, in this example, worn as a watch. The medical implant information reporting device 20 displays information about the medical implant controller and battery 18 and pump 16 that it receives wirelessly from the implant controller 18 and/or the external controller 14. In one configuration, the reporting device 20 may display, for example, the remaining time of operation of the pump 16 with power from implanted controller and battery 18 when the patient is not wearing external TETS coil 12 and external controller and battery 14 and the power output and flow generated by the VAD and may further generate an alert indication suction or occlusion conditions of the VAD. The medical implant information reporting device 20 has a rechargeable battery that is trickle-charged by electromagnetic energy from the source coil 12 that induces current in a harvesting coil integrated with the medical implant information reporting device 20

Figure 2:
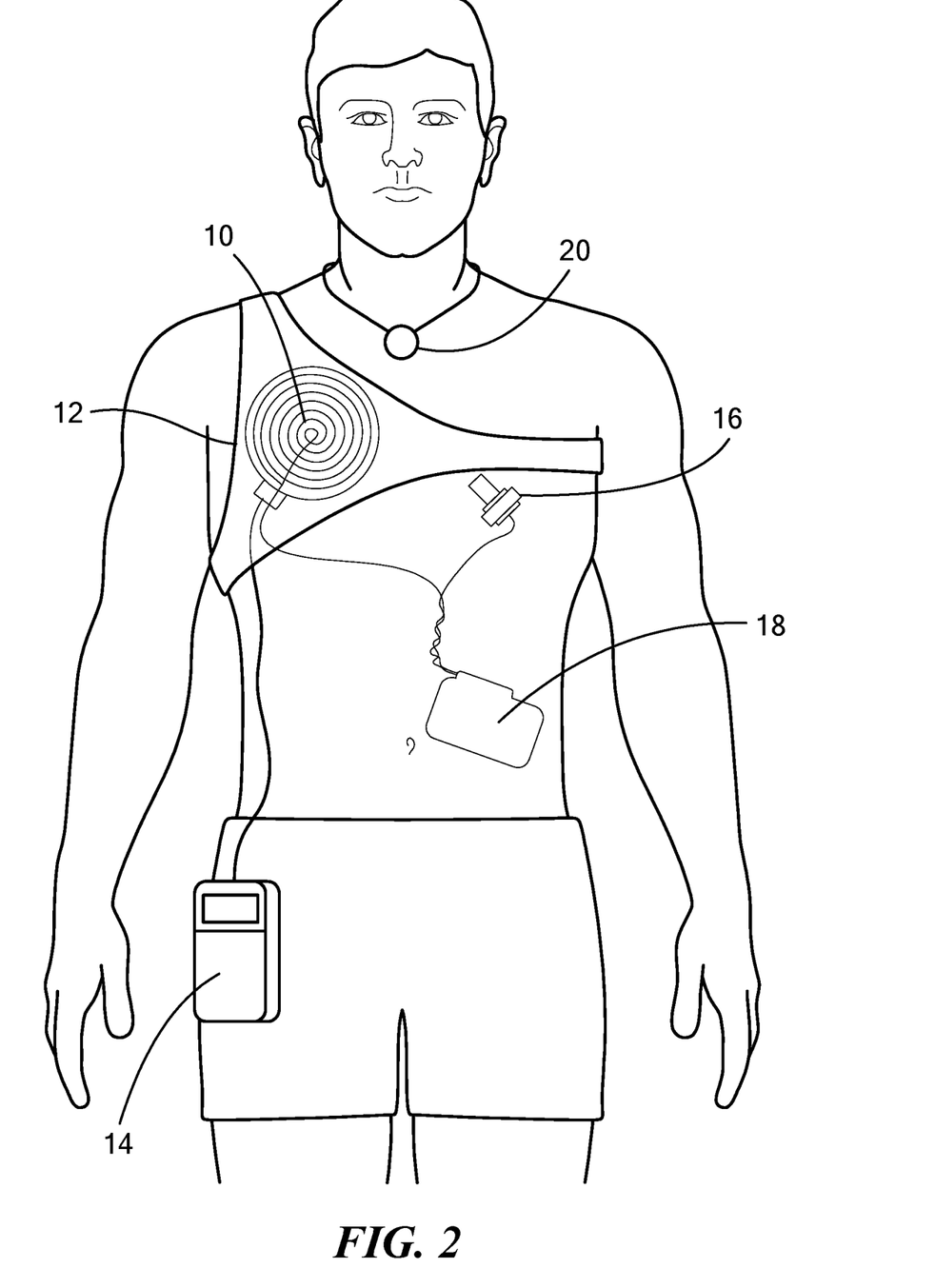
FIG. 2 depicts a second configuration of a TETS with a medical implant information reporting device worn as a pendant.

Referring now to FIG. 2 which illustrates a first configuration of a TETS with a medical implant information reporting device worn as a pendant. There are two differences between the embodiments of FIGS. 1 and 2. First, in FIG. 1, the external coil 12 is wrapped around the torso of the patient, whereas, in FIG. 2, the external coil 12 is positioned on the chest of the patient. Second, in FIG. 1, the reporting device 20 is worn as a watch, whereas in FIG. 2, the reporting device 20 is worn as a pendant in close proximity to the external coil 12.

Figure 3:
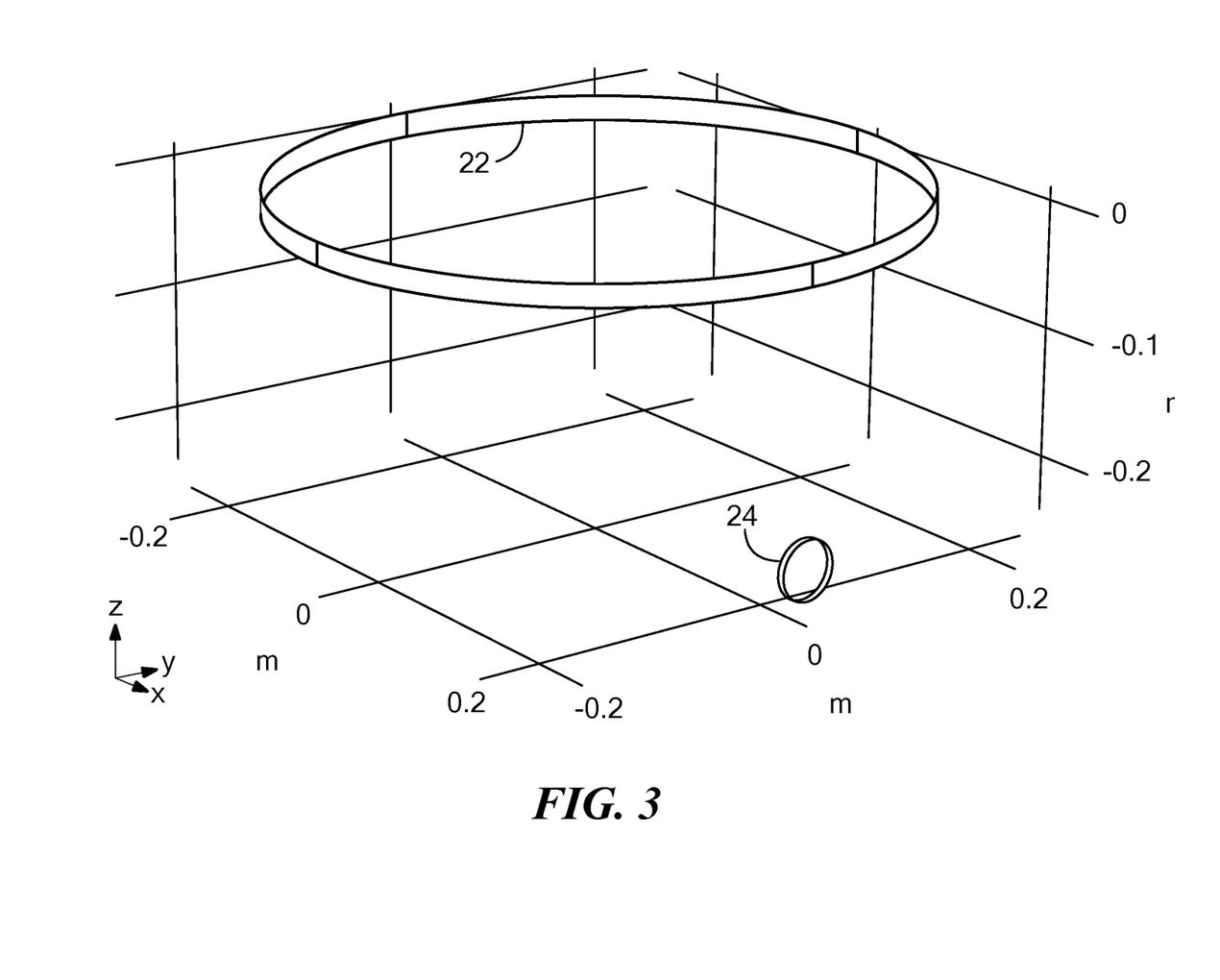
FIG. 3 is model of a source coil and a harvesting coil constructed in accordance with the principles of the present application for a wrist watch case.
Figure 4:
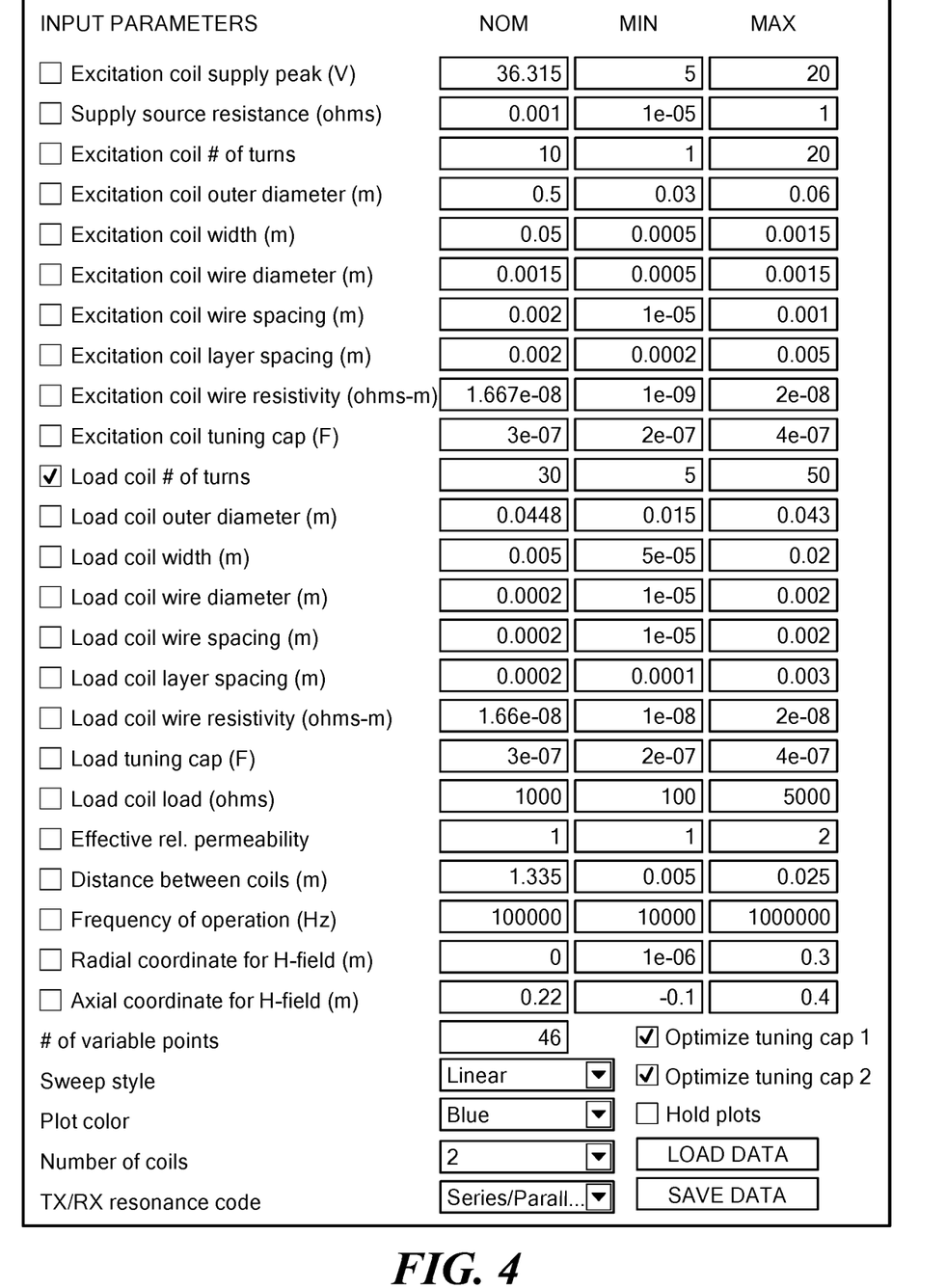
FIG. 4 is a table of parameters for design exercise of a harvesting coil sufficient to couple enough energy from the source coil to charge the medical implant information reporting device in the form of a wrist watch.

Referring now to FIG. 3 which illustrates a configuration of a source coil 22, which is the external coil 12 of FIGS. 1 and 2, and a harvesting coil 24 inside a watch or pendant to receive power from the source coil 22 to power the implant information reporting device 20. FIG. 4 is a table of parameters utilized in an exemplary design iteration to configure the source coil (excitation coil) 22 and the harvesting coil (load coil) 24. Some of the parameters may be adjusted to find an optimum design of the harvesting coil include: number of turns, wire diameter, spacing between turns, outer diameter. Other parameters include distance between the coils 22 and 24 and frequency of operation and resonance configuration of coil 24.

Figure 5:
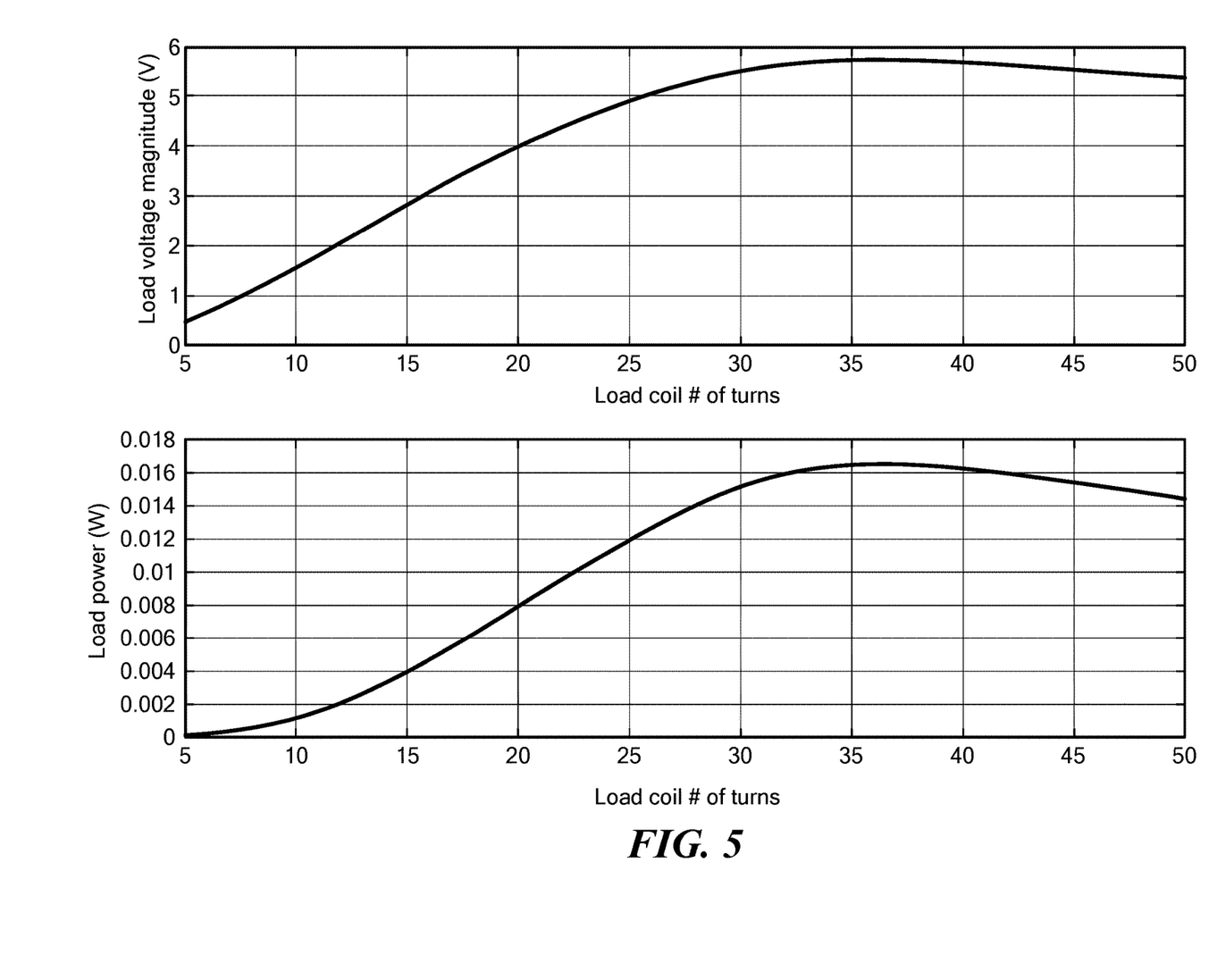
FIG. 5 shows two curves: one for delivered load voltage and one for delivered load power, each as a function of number of turns of the harvesting coil for a wrist watch case.

Referring now to FIG. 5 which shows two computer generated curves; one for delivered load voltage and one for delivered load power, each as a function of number of turns of the harvesting coil 24 in an exemplary configuration. A maximum voltage and power are achieved when the number of turns of the harvesting coil 24 is about 35, although any number of turns may be utilized in the harvesting coil ranging 5-200 depending on coil size, operating frequency. Thus, the source coil provides the electrical energy to the harvesting coil to trickle charge the battery of the medical implant information reporting device.

To determine the parameters of the harvesting coil 24, the parameters of a Samsung® Gear II device were assumed as an example parameters of a medical implant information reporting device 20. This device has a 300 milli-Ampere-hour rechargeable battery that may typically last 4 days for an average current drain of 3 milli-Amperes. From these and an average battery voltage of 3 volts assumption, an average power consumption of 9 milli-Watts and an effective load resistance of 1 kilo-Ohm are derived. With these assumptions, the inductive coupling between the source coil 22 and the harvesting coil 24 should be capable of generating greater than 9 milli-Watts at the harvesting coil 24. In one configuration, power generated by the harvesting coil 24 is greater than 16 milli-Watts for a 1 kilo-Ohm load, thus generating excess power to trickle-charge the battery of the reporting device.

In one design exercise there is assumed a case when the source coil is transferring 10 Watts of power delivered to the implant, generating a 17.8 micro-Tesla B-field or a 14.16 Amperes/meter H-field at the center of the wrist harvesting coil.

Figure 6:
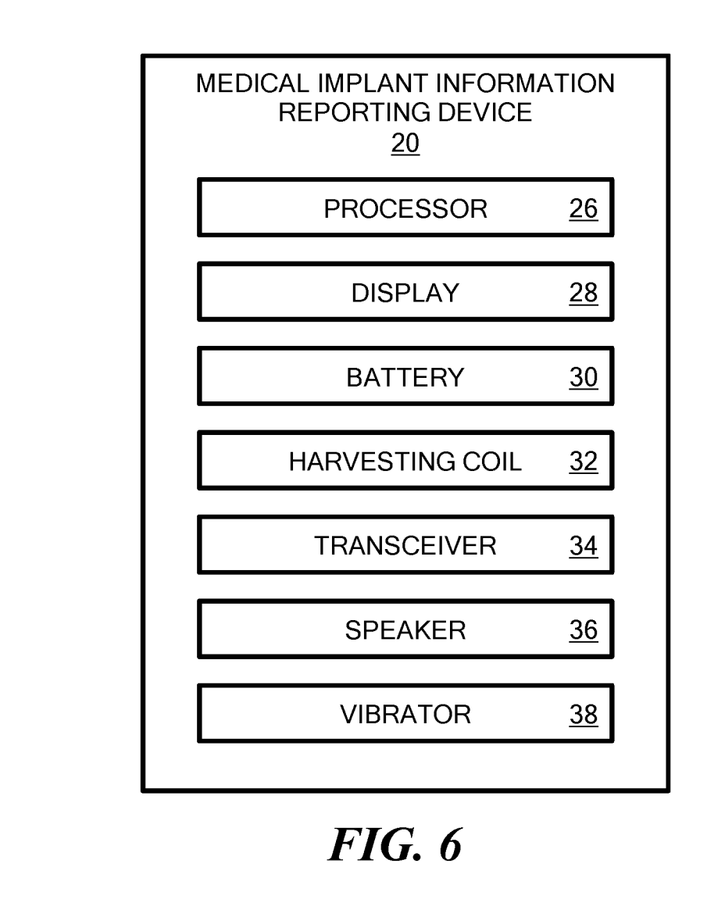
FIG. 6 is a block diagram of a medical implant information reporting device constructed in accordance with principles disclosed herein.

Referring now to FIG. 6 in which block diagram of a medical implant information reporting device 20 is shown. The reporting device 20 includes a processor 26 configured to process information concerning one of the implant device 16, the implanted controller and battery 18 and the external controller and battery 14. Such information may include a status of operation of the implant device 16, and a level of charge of a battery of the controller and battery 14 and/or 18. A display 28 may be configured to display this information. A battery 30 is configured to provide power to the processor 26 and the display 28. The battery is charged by the harvesting coil 32. The information to be processed and displayed may be received wirelessly by a transceiver 34 which is also powered by the battery 30. The medical implant information reporting device 20 may also include a speaker 36 to sound an audio alert or spoken message to the patient, the message optionally including system status information, and/or a vibrator 38 to, for example, provide haptic feedback to alert patient if the audio alert is missed due to thick clothing or noise in the environment.

Figure 7:
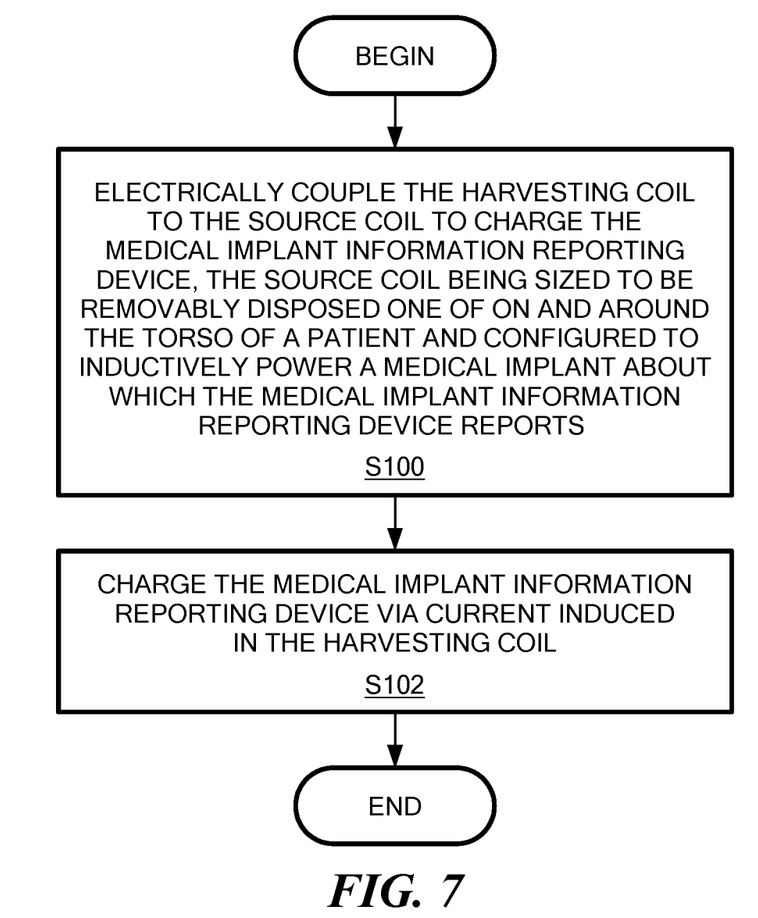
FIG. 7 is a flowchart of an exemplary process for charging a medical implant information reporting device.

FIG. 7 is a flowchart of an exemplary process for charging a medical implant information reporting device 20. The process includes electrically coupling the harvesting coil 24, 32 to the source coil 22, to charge the medical implant information reporting device 20, where the source coil 22, is sized to be removably disposed one of on and around the torso of a patient and configured to inductively power a medical implant 16 about which the medical implant information reporting device reports (block S100). The process also includes trickle-charging the medical implant information reporting device 20 via current induced in the harvesting coil 24, 32 (block S102).

Figure 8:
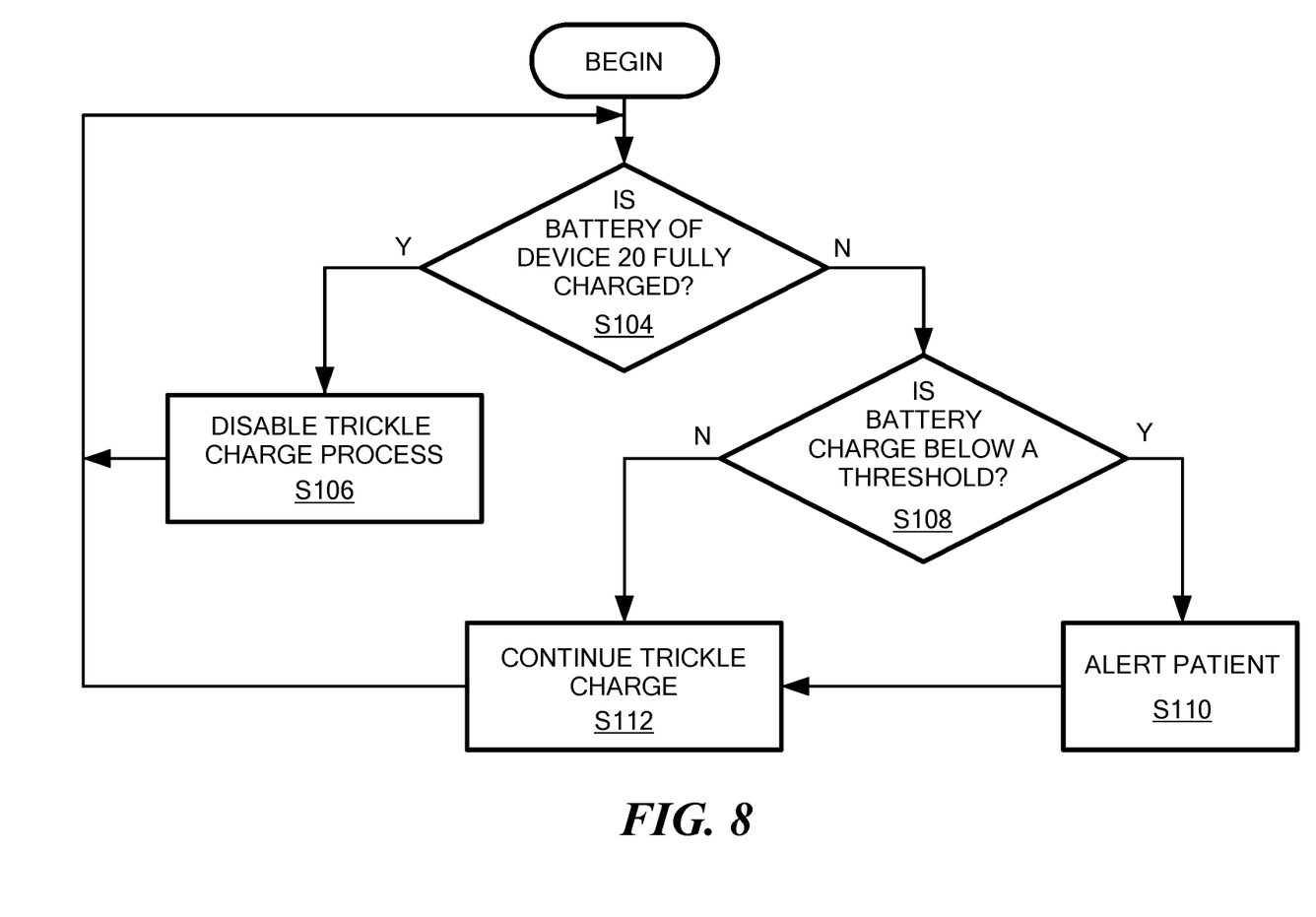
FIG. 8 is a flowchart of an exemplary process for charging a medical implant information reporting device.

FIG. 8 is a flowchart of an exemplary process for charging a medical implant information reporting device 20. The process includes determining if the battery of the medical implant information reporting device 20 is fully charged (block S104). If so, the trickle charge process is disabled (block S106), which discontinues charging of the battery of the device 20. If the battery of the device 20 is not fully charged, a determination is made whether the battery charge is below a threshold (block S108). If so, the patient is alerted to the low battery charge condition (block S110). This gives the patient the option of repositioning the device 20 or charging the battery of the device 20 with an external charger if for some reason, inductive coupling from the TETS coil is failing. This external recharge device may be another inductively coupled recharge system similar to those for recharging smart phones. If the battery charge is above the threshold, the trickle charge process continues (block S112).

Thus, according to one aspect, some embodiments include a method for charging a medical implant information reporting device having an integrated harvesting coil configured to couple energy from an electromagnetic field of a source coil to induce current in the harvesting coil. The method includes electrically coupling the harvesting coil to the source coil to charge the medical implant information reporting device, the source coil being sized to be removably disposed one of on and around the torso of a patient and configured to inductively power a medical implant about which the medical implant information reporting device reports.

According to this aspect, in some embodiments, the source coil is configured to charge the medical implant information reporting device at a distance between the source coil and the harvesting coil exceeding 20 centimeters. In some embodiments, the source coil is configured to charge the medical implant information reporting device at a distance between the source coil and the harvesting coil exceeding 1 meter, for example, for the case in FIG. 1 where source coil is large. In some embodiments, the source coil generates power to produce an electromagnetic field having a magnetic field strength exceeding 15 micro-Tesla at the harvesting coil of the medical implant information reporting device. In some embodiments, the harvesting coil is configured to generate more than 15 milli-Watts of power delivered to a 1 kilo-ohm load. In some embodiments, the harvesting coil has from 5 to 200 turns and an outer diameter from 1 to 6 centimeters. In some embodiments, the medical implant information reporting device is wearable as one of a watch on a wrist, a pendant that hangs from a neck and an armband worn over an upper arm of a patient having the medical implant.

In some embodiments, a medical implant information reporting device having an integrated harvesting coil configured to couple energy from an electromagnetic field of a source coil, to induce current in the harvesting coil is provided. The reporting device includes a display configured to display information about a medical implant. The reporting device may include a speaker or vibrator configured to relay spoken messages or alert sounds or vibrations regarding the status of the implanted system. The reporting device also includes the harvesting coil embedded in the medical implant information reporting device, the harvesting coil being configured to couple energy from the source coil to charge a battery of the medical implant information reporting device.

According to this aspect, in some embodiments, the harvesting coil is configured to receive power to charge the medical implant information reporting device at a distance between the source coil and the harvesting coil exceeding 1 meter. In some embodiments, the harvesting coil is configured to charge the medical implant information reporting device upon receiving an electromagnetic field having a magnetic field strength not exceeding about 15 micro-Tesla at the harvesting coil of the medical implant information reporting device. In some embodiments, the harvesting coil is configured to generate more than 15 milli-Watts of power delivered to a 1 kilo-ohm load. In some embodiments, the harvesting coil has from 5 to 200 turns and an outer diameter from 1 to 6 centimeters to achieve coupling of energy from the source coil to charge the battery.

In some embodiments, a medical implant information reporting device configured for operation with a transcutaneous electrical transmission subsystem (TETS) of a ventricular assist device (VAD), the TETS having a source coil configured to provide energy to the VAD is provided. The reporting device includes a harvesting coil integrated with the reporting device, the harvesting coil having a number of turns, diameter and conductor thickness to couple energy from the source coil of the TETS to charge a battery of the reporting device. The reporting device also includes a rechargeable battery configured to be recharged by current from the harvesting coil and a display configured to display information concerning the VAD.

In some embodiments, the medical implant information reporting device further includes a speaker and/o vibrator to sound an alert and/or vibrations if the charge of the battery is less than a threshold. In some embodiments, the harvesting coil is configured to provide power to the reporting device to enable an average power consumption by the reporting device exceeding 8 milli-Watts. In some embodiments, the reporting device presents to the harvesting coil an effective load resistance of between 0.8 to 10 kilo-Ohms. In some embodiments, the battery is rechargeable when a distance is between the source coil and the harvesting coil exceeds 20 centimeters.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for charging a medical implant information reporting device having an integrated harvesting coil configured to couple energy from an electromagnetic field of a source coil to induce current in the harvesting coil, the method comprising:
   electrically coupling the harvesting coil to the source coil to trickle-charge the medical implant information reporting device, the source coil being sized to be non-circumferentially removably disposed on only a portion of a chest of a patient and configured to inductively power a medical implant about which the medical implant information reporting device reports.

2. The method of claim 1, wherein the source coil is configured to charge the medical implant information reporting device at a distance between the source coil and the harvesting coil exceeding 5 centimeters.

3. The method of claim 1, wherein the source coil is configured to charge the medical implant information reporting device at a distance between the source coil and the harvesting coil exceeding 1 meter.

4. The method of claim 1, wherein the source coil generates power to produce an electromagnetic field having a magnetic field strength exceeding 15 microTesla at the harvesting coil of the medical implant information reporting device.

5. The method of claim 1, wherein the harvesting coil is configured to generate more than 15 milli-Watts of power delivered to a 1 kilo-ohm load.

6. The method of claim 1, wherein the harvesting coil has from 5 to 200 turns and an outer diameter from 1 to 6 centimeters.

7. The method of claim 1, wherein the medical implant information reporting device is wearable as one from the group consisting of a watch on a wrist and a pendant that hangs from a neck of a patient having the medical implant.

8. A medical implant information reporting device having an integrated harvesting coil configured to couple energy from an electromagnetic field of a source coil to induce current in the harvesting coil, comprising:
   at least one of a display configured to display information about a medical implant and a speaker configured to provide acoustic messages about the medical implant; and
   the harvesting coil embedded in the medical implant information reporting device, the harvesting coil being configured to couple energy from the source coil configured to be non-circumferentially disposed on only a portion of a chest of a patient to charge a battery of the medical implant information reporting device, the medical implant information reporting device being a pendant.

9. The device of claim 8, wherein the harvesting coil is configured to receive power to charge the medical implant information reporting device at a distance between the source coil and the harvesting coil exceeding ½ meter.

10. The device of claim 8, wherein the harvesting coil is configured to charge the medical implant information reporting device when receiving an electromagnetic field having a magnetic field strength not exceeding 15 micro-Tesla at the harvesting coil of the medical implant information reporting device.

11. The device of claim 8, wherein the harvesting coil is configured to generate more than 15 milli-Watts of power delivered to a 1 kilo-ohm load.

12. The device of claim 8, wherein the harvesting coil has from 5 to 200 turns and an outer diameter from 1 to 6 centimeters to achieve coupling of energy from the source coil to charge the battery.

13. A medical implant information reporting device configured for operation with a transcutaneous electrical transmission subsystem (TETS) of a ventricular assist device (VAD), the TETS having a source coil configured to provide energy to the VAD, the reporting device comprising:

a harvesting coil integrated with the reporting device, the harvesting coil having a plurality of turns, diameter, and conductor thickness to couple energy from the source coil of the TETS to trickle-charge a battery of the reporting device, the source coil being configured to be non-circumferentially disposed on only a portion of a chest of a patient;

and at least one of a display configured to display information concerning the VAD, a speaker to provide acoustic information concerning the VAD, and a vibrator to provide haptic feed concerning the VAD.

14. The reporting device of claim 13, wherein the source coil is configured to provide power to the VAD.

15. The reporting device of claim 13, wherein the speaker is further configured to sound an alert if the charge of the battery is less than a threshold and the vibrator is configured to vibrate if the charge of the battery is less than the threshold.

16. The reporting device of claim 13, wherein the harvesting coil is configured to provide power to the reporting device to enable an average power consumption by the reporting device exceeding 8 milli-Watts.

17. The reporting device of claim 13, wherein the reporting device presents to the harvesting coil an effective load resistance of between 0.8 to 10 kilo-Ohms.

18. The reporting device of claim 13, wherein the battery is rechargeable when a distance is between the source coil and the harvesting coil exceeds 5 centimeters.

19. The reporting device of claim 13, wherein the reporting device is a pendant.

* * * * *